United States Patent [19]

Roessler et al.

[11] Patent Number: 4,762,521
[45] Date of Patent: Aug. 9, 1988

[54] ABSORBENT GARMENT WITH QUILTED AND CONFORMABLE ABSORBENT PAD

[75] Inventors: Thomas H. Roessler, Menasha; Dan D. Endres, Appleton; Kenneth M. Enloe, Neenah; Andrew E. Huntoon, Appleton; Mary E. Lippert, Hortonville, all of Wis.

[73] Assignee: Kimberly-Clark Corporation, Neenah, Wis.

[21] Appl. No.: 851,027

[22] Filed: Apr. 11, 1986

[51] Int. Cl.4 .............................................. A61F 13/16
[52] U.S. Cl. ..................... 604/38 SA; 604/38 SR; 604/380; 604/389; 604/366; 604/383
[58] Field of Search ................... 604/385.1, 385.2, 358, 604/366, 369, 378, 380, 366

[56] References Cited

U.S. PATENT DOCUMENTS

| 3,245,407 | 4/1966 | Mason | 128/284 |
|---|---|---|---|
| 3,441,024 | 4/1969 | Ralph | 128/287 |
| 3,682,761 | 8/1972 | Lee et al. | 161/124 |
| 3,749,627 | 7/1973 | Jones, Sr. | 156/268 |
| 3,776,233 | 12/1973 | Schaar | 604/385.1 |
| 3,860,003 | 1/1975 | Buell | 128/287 |
| 3,889,679 | 6/1975 | Taylor | 604/385.1 |
| 3,927,673 | 12/1975 | Taylor | 128/287 |
| 3,965,906 | 6/1976 | Karami | 604/366 |
| 3,973,291 | 8/1976 | Kolbach | 19/148 |
| 3,994,299 | 11/1976 | Karami | 604/366 |
| 4,000,028 | 12/1976 | Hoey | 604/366 |
| 4,027,672 | 6/1977 | Karami | 604/385.1 |
| 4,036,233 | 7/1977 | Kozak | 604/385.2 |
| 4,050,462 | 9/1977 | Woon et al. | 604/385.1 |
| 4,326,528 | 4/1982 | Ryan et al. | 128/287 |
| 4,333,979 | 6/1982 | Sciaraffa et al. | 604/366 |
| 4,355,066 | 10/1982 | Newman | 604/366 |
| 4,388,056 | 6/1983 | Lee et al. | 425/83.1 |
| 4,388,075 | 6/1983 | Mesek et al. | 604/385 |
| 4,501,587 | 2/1985 | Enloe | 604/385.1 |
| 4,515,595 | 5/1985 | Kievit et al. | 604/385 |
| 4,548,604 | 10/1985 | Ellsworth | 604/385.2 |

FOREIGN PATENT DOCUMENTS 0157649 10/1985 European Pat. Off. ........ 604/385 R

Primary Examiner—C. Fred Rosenbaum
Assistant Examiner—Denise Whelton
Attorney, Agent, or Firm—Paul Yee

[57] ABSTRACT

The present invention provides a distinctive absorbent garment which comprises a backsheet having waistband portions at each longitudinal end thereof, and intermediate portion interconnecting the waistband portions, and marginal portions along each lateral side edge of the backsheet. A liquid permeable liner sheet is located in facing relation with the backsheet, and an absorbent body is located between the backsheet and liner sheet. The absorbent body delimits waistband sections at each longitudinal end thereof, delimits an intermediate section interconnecting the waistband sections, and delimits a marginal contour at each lateral side edge of the absorbent body. Each marginal side contour has at least one collapsible notch section formed therein. A fastening mechanism is connected to the garment for securing the garment on a wearer.

20 Claims, 4 Drawing Sheets

ABSORBENT GARMENT WITH QUILTED AND CONFORMABLE ABSORBENT PAD

FIELD OF THE INVENTION

The present invention is related to disposable absorbent garments, such as diapers, incontinent garments, sanitary napkins, and the like. More particularly, the present invention relates to a disposable absorbent garment which is more readily conformable to the body shape of a wearer and includes a quilted absorbent pad. This absorbent garment has improved absorbency characteristics and a more form-fitting appearance.

BACKGROUND OF THE INVENTION

Disposable absorbent garments, such as diapers, incontinence garments, and the like, have become popular because of their effectiveness in absorbing body exudates and because of their convenience. Considerable effort, however, has been expended to improve the absorbency characteristics of the garment. For example, elasticized legbands have been employed to reduce leakage from the garment crotch area. Various conventional types of elastic legband configurations are shown in U.S. Pat. No. 3,860,003 issued Jan. 14, 1975 to K. Buell; U.S. Pat. No. 4,050,462 issued Sept. 27, 1977 to L. S. Woon, et al.; U.S. Pat. No. 4,388,075 issued June 14, 1983 to F. Mesek, et al.; and U.S. Pat. 4,326,528 issued Apr. 27, 1982 to L. Ryan.

Elasticized waistbands have also been employed to further improve that appearance and effectiveness of a disposable absorbent garment. For example, elasticized waistbands are described in U.S. Pat. No. 3,245,407 issued Apr. 12, 1966 to A. Mason and U.S. Pat. No. 4,515,595 issued May 7, 1985 to D. Kievit.

Conventional absorbent garments have also included contoured absorbent pads in which greater amounts of absorbent material have been selectively located in those "target" areas that receive greater quantities of body exudates. Examples of contoured, absorbent pads are shown in U.S. Pat. No. 4,388,056 issued July 14, 1983 to F. Lee, et al.; U.S. Pat. No. 3,682,761 issued Aug. 8, 1972 to C. Lee, et al.; and U.S. Pat. No. 3,973,291 issued Aug. 10, 1976 to C. Kolbach.

The absorbent pads employed with disposable, absorbent garments have been selectively configured with perforations or apertures to help direct liquids away from the body of the wearer and into the absorbent material. Examples of perforated or apertured absorbent pads are described in U.S. Pat. No. 3,441,024 issued Apr. 29, 1969 to H. Ralph; U.S. Pat. No. 3,749,627 issued July 31, 1973 to J. Jones, Sr.; U.S. Pat. No. 3,889,679 issued July 17, 1975 to G. Taylor; and U.S. Pat. No. 3,927,673 issued Dec. 23, 1975 to G. Taylor.

Conventional disposable, absorbent garment designs, such as those described above, have not been completely satisfactory. The amount of absorbent material that can be located within the garment crotch section is limited because of the restricted, narrow space between the wearer's legs. In addition, the effectiveness of the conventional disposable garment with regard to containing body exudates has not been completely satisfactory. Discharges of the exudates have not been readily absorbed or contained by the absorbent garment, and as a result, the exudates, particularly feces, can undesirably leak out and soil the outer clothes of the wearer. A factor which contributes to the undesired leakage of fecal matter is that high absorbency garments containing relatively large amounts of absorbent material have not been readily conformable to the body shape of the wearer because of the bulk, stiffness and shape of the absorbent pads. As a result, body exudates can undesirably migrate and leak past the elasticized legbands before the exudates can be absorbed or otherwise contained by the absorbent material in the garment.

BRIEF DESCRIPTION OF THE INVENTION

The present invention provides a distinctive absorbent garment which includes a backsheet having waistband portions at each longitudinal end thereof, an intermediate portion interconnecting the waistband portions, and marginal portions along each lateral side edge thereof. A liquid permeable liner sheet is located in facing relation with the backsheet, and an absorbent body is located between the backsheet and liner sheet. The absorbent body delimits waistband sections at each longitudinal end thereof, delimits an intermediate section interconnecting the waistband sections, and delimits a marginal contour at each lateral side edge thereof. In addition, each marginal side contour has at least one collapsible notch section formed therein. A fastening means is included for securing the garment on a wearer.

The distinctive absorbent garment configuration provided by the present invention can advantageously increase the absorbency effectiveness of the garment. The absorbent garment can also be more conformable to the body of the wearer and as a result, the garment can have greater resistance to leakage and can present a more form fitting appearance.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The following detailed description of the invention will be made in the context of a disposable diaper garment. However, it will be readily apparent that the structural configurations of the present invention can also be incorporated into other absorbent garments, such as incontinence garments, sanitary napkins and the like. All of such adaptations are contemplated as being within the scope of the present invention.

Figure 1:
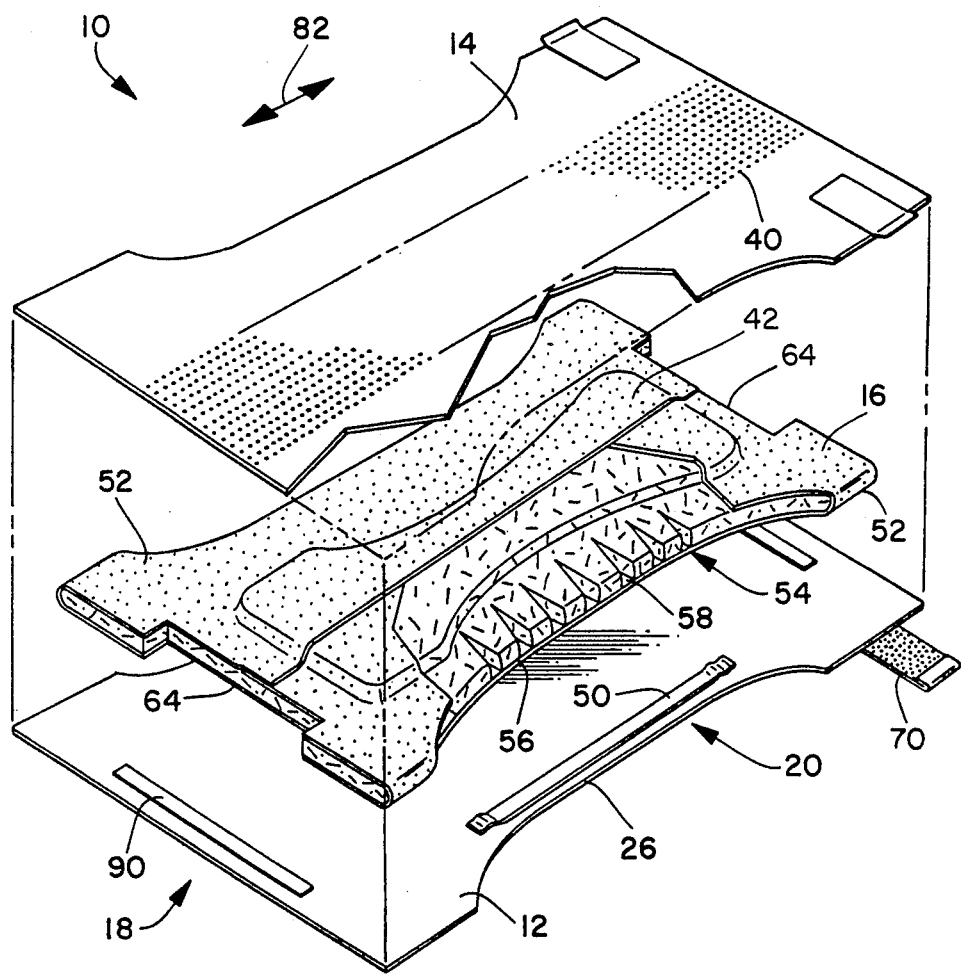
FIG. 1 shows an exploded isometric view of a representative absorbent garment.

Referring now to FIG. 1, an absorbent garment, such as disposable diaper 10, includes a backsheet 12 having waistband portions 18 at each longitudinal end thereof. An intermediate portion 20 interconnects the waistband portions, and marginal portions 26 are located along each lateral side edge thereof. A liquid permeable liner sheet 14 is located in facing relation with backsheet 12, and an absorbent body 16 is located between backsheet 12 and liner sheet 14. The absorbent body delimits absorbent waistband sections 52 at each longitudinal end thereof and an absorbent intermediate section 54 which interconnects the waistband sections. In addition, the absorbent body delimits a marginal side contour 56 at each lateral side edge thereof. Each marginal side contour 56 is interrupted by at least one collapsible notch section 58 formed therein. Fastening means, such as pressure-sensitive tape fasteners 70, are constructed and arranged for securing the garment on a wearer. In addition, leg elastic members 50 are located adjacent to the side edges of absorbent body 16, and extend generally along the longitudinal direction 82 of the garment. The leg elastics are spaced a selected distance from the edges of absorbent body 16 and are suitably attached to the side margins 26 of either or both of backsheet 12 and liner sheet 14. Leg elastics 50 are also suitably configured and arranged to provide elasticized gathers at the garment intermediate section to help reduce the leakage of fluids around the leg and crotch areas of the wearer.

Figure 2:
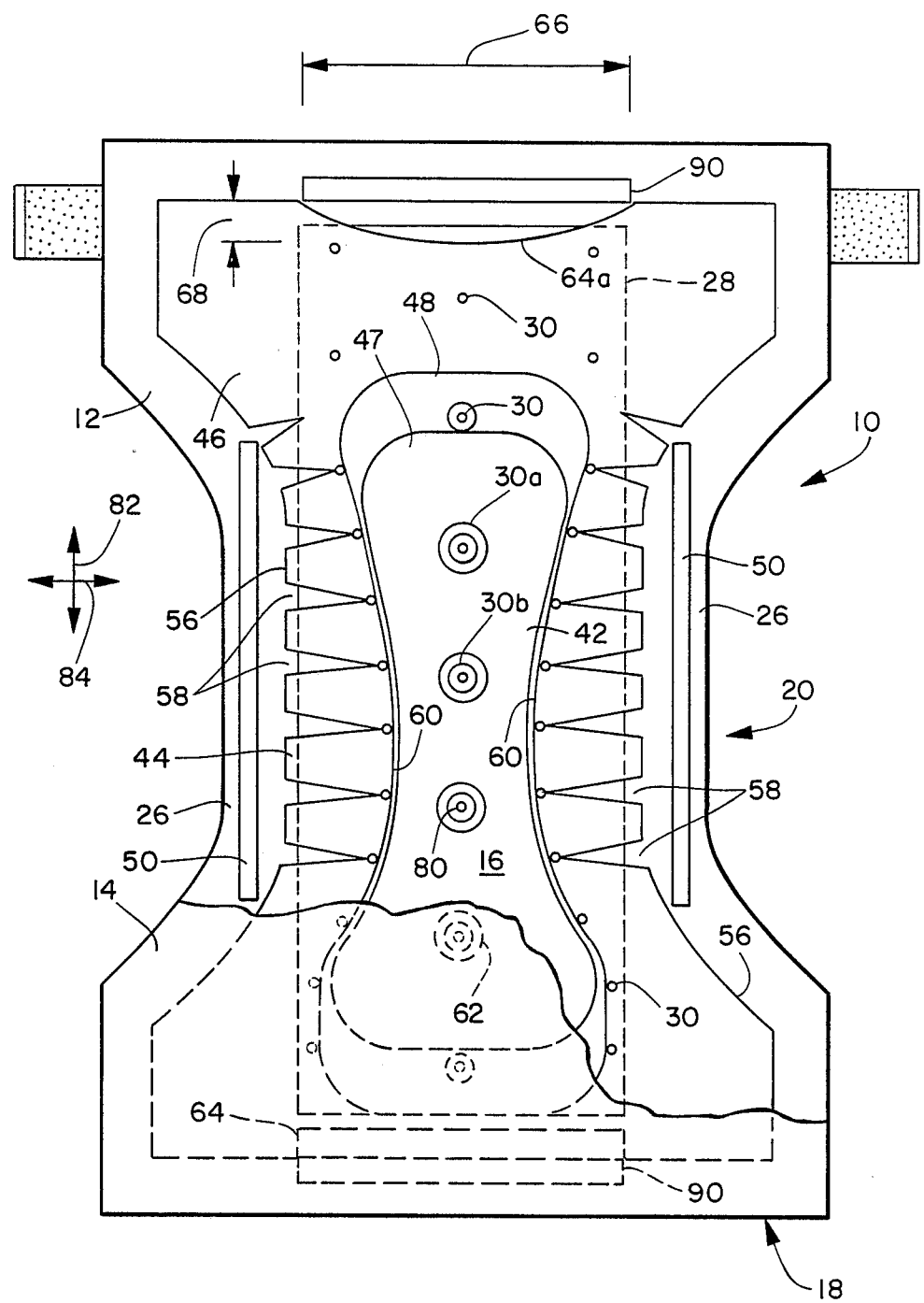
FIG. 2 representatively shows a top, plan view of another embodiment of the disposable absorbent garment of the invention.
Figure 3:
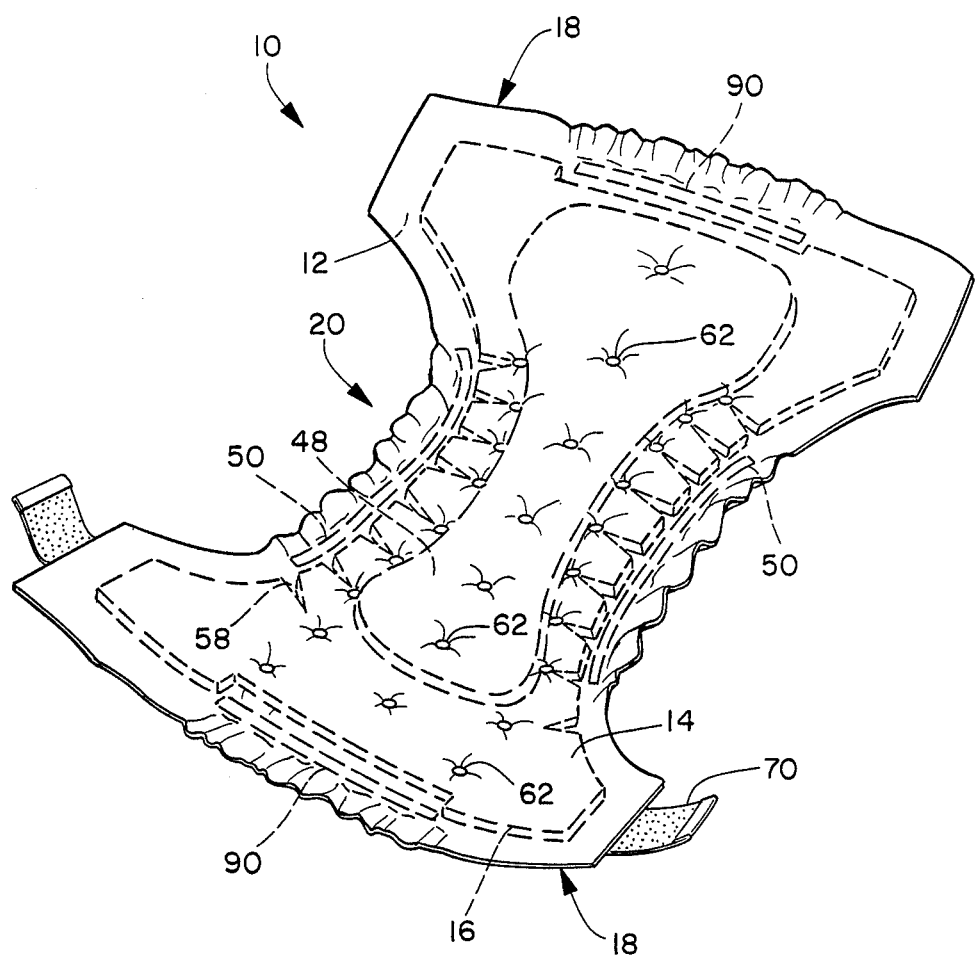
FIG. 3 shows a perspective view of a garment of the invention.

In one aspect of the invention representatively shown in FIG. 2, liner sheet 14 is composed of a thermally fusible material. In addition, the absorbent garment further comprises a bonding layer 28 which is located between backsheet 12 and absorbent body 16, and which is also composed of a thermally fusible material. Absorbent body 16 has a plurality of depressions or apertures 30 formed at least partially therethrough, and liner sheet 14 is fusibly interconnected to bonding layer 28 through these apertures. This particular configuration advantageously provides funnel pockets 62 which help draw and conduct liquids, such as urine, away from the wearer's body and help contain semi-solid material, such as fecal matter.

In another aspect of the invention, liner sheet 14 need not be composed of a fusible material, and bonding sheet 28 may optionally be eliminated. In addition, absorbent body 16 has a plurality of apertures formed at least partially therethrough. With this arrangement, liner sheet 14 is adhesively or mechanically interconnected through the apertures to backsheet 12, or optionally to bonding sheet 28, thereby producing funnel pockets 62. Bonding sheet 28 may or may not be composed of a fusible material when employing this particular configuration of the invention.

In yet another aspect of the invention, at least a portion of absorbent body 16 is composed of a material which contains a thermally fusible component, such as coform material. In this configuration, a thermally fusible liner sheet 14 is positioned through the apertures formed in absorbent body 16, and is fusibly interconnected with the fusible material in the absorbent body to form funnel pockets 62. For example, the apertures in absorbent body 16 may extend partially therethrough and terminate at a layer or other region of fusible coform material. Liner sheet 14 can then be positioned into the apertures and be fusibly bonded to the coform layer of the absorbent body.

Apertures 30 have been described in the context of discrete holes or openings formed into absorbent body 16. Equivalent apertures or depressions, however, can be produced by compressing limited regions of the absorbent body and bonding or otherwise holding the fibers of the absorbent body material to retain the aperture configuration. For example, the absorbent body may comprise regions composed of thermally fusible material, and the liner sheet may be forcibly displaced into the absorbent body to form a depressed pocket region. The liner sheet may then be fusibly bonded to the compressed absorbent body material. This bonding operation attaches the liner sheet to the compressed absorbent body material and also interconnects the fusible fibers within the absorbent body to hold and maintain the desired funnel pocket configuration.

Diaper 10 can be rectangular or T-shaped, but preferably has a generally "hour-glass" shape or a I-shape as representatively shown in the figures. As a result, the diaper delimits waistband sections at each of its two longitudinal ends and an intermediate section which interconnects the two waistband sections and defines a generally narrower crotch section of the garment. These diaper waistband and intermediate sections substantially correspond to the waistband and intermediate sections of backsheet 12. During use, the two waistband sections effectively encircle the waist of the wearer, with one waistband section spanning across the "front" side of the wearer and the other waistband section spanning across the "rear" or back side of the wearer. The ear-like flaps at the lateral side edges of the waistband sections would then overlap at the sides of the wearer and would be secured with tape fasteners 70. A portion of the diaper intermediate section passes between the legs and covers the crotch of the wearer.

Backsheet 12 is preferably composed of a liquid impermeable material to protect the outer clothing of the wearer from soiling. Suitable materials for producing backsheet 12 include polyolefin films, such as polyethylene and polypropylene films. Other conventional, liquid impermeable film materials may also be employed.

In the shown embodiment, liner sheet 14 is generally coextensive with backsheet 12 and is composed of a liquid permeable material. The liner sheet allows a relatively free passage of liquid therethrough and helps to maintain a relatively dry surface against the wearer's skin. Typically, liner sheet 14 is composed of a porous, nonwoven material, such as spunbond material composed of polyolefin filaments. Suitable filaments for the spunbond material include, for example, polyethylene and polypropylene filaments. Liner sheet 14 can be attached in a superposed, facing relation onto absorbent body 16 with suitable bonding means, such as a hot melt adhesive. The liner is also bonded to backsheet 12 along the contacting portions of the side margins and end margins of the liner and backsheet. The liner sheet may also include apertures 40 to facilitate the passage of viscous, semi-solid materials, such as feces, therethrough. A representative apertured liner sheet 14 is illustrated in FIG. 1. As previously discussed, liner sheet 14 is preferably composed of a thermally fusible material. This arrangement allows an attachment of the liner sheet to other parts of the garment employing thermal bonds, such as sonic bonds.

Absorbent body 16 is interposed in facing relationship between backsheet 12 and liner sheet 14, and typically comprises a pad of absorbent material, such as tissue wadding or wood pulp fibers. In the illustrated embodiment, the absorbent pad comprises a web of absorbent cellulosic fibers, commonly referred to as "fluff". The absorbent body can optionally be composed of a coform material which comprises a mixture of cellulosic fibers and polymeric fibers, such as polyethylene and polypropylene fibers. The polymeric fibers provide a fusible component within absorbent body 16 which can be employed to form thermal bonds with other elements of the garment. One or more layers of tissue wrap material may extend around and enclose the cellulosic fluff pad. This tissue wrap may be at least partially composed of a fusible material, such as polyolefin fibers. When the tissue wrap includes fusible material, the tissue wrap can comprise fusible bonding sheet 28 of the garment structure.

Absorbent body 16 can also include selected quantities of superabsorbent materials, such as avar gum, pectin and hydrogel superabsorbent materials. Such superabsorbent materials include inorganic and organic compounds capable of absorbing aqueous fluids and retaining them under moderate pressures. For good results, the superabsorbent materials should be substantially water insoluble. Suitable hydrogels include, for example, inorganic materials, such as silica gels, and organic compounds, such as cross-linked polymers. Cross-linking may be by covalent, ionic, Van der Waals, or hydrogen bonding. Examples of suitable polymers include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, polyacrylates, and isobutylene maleic anhydride copolymers, and mixtures thereof.

Absorbent body 16 may also have a contoured thickness profile in which the medial portion 42 of the absorbent body has a greater amount of absorbent material than the marginal portions 44 of the absorbent body. In the embodiment representatively shown in FIGS. 2 and 4, absorbent body 16 has a generally stepped cross-sectional contour. As a result, the absorbent body comprises multiple thickness zones, such as zones defined by absorbent layers 46, 47 and 48.

Primary absorbent layer 46 delimits and defines waistband sections at each longitudinal end thereof, and defines an intermediate section which interconnects the waistband sections. The absorbent body waistband and intermediate sections approximately correspond to the waistband and intermediate sections of backsheet 12. As illustrated in FIG. 2, primary absorbent layer 46 further delimits and defines a general marginal contour 56 at each lateral side edge of absorbent body 16. Each marginal side contour 56 is interrupted by at least one collapsible notch section 58 which is formed into each side margin 44 of the absorbent body. In the shown embodiment, a plurality of collapsible notches 58 is formed into and interrupts each of the absorbent body, side contours 56. Collapsible notches 58 advantageously reduce the stiffness of the lateral side margins 44 of the primary absorbent layer, and allow the layer of absorbent material to more easily flex and articulate as notches 58 close and open. As a result, side margins 44 of the absorbent body can be more conformable around the legs and through the crotch area of the wearer. This greater conformability can improve the appearance of the garment during use, and can better allow leg elastics 50 to form a closer, more effective seal around the legs of the wearer, thereby reducing the leakage of fluids from the garment leg areas.

The illustrated embodiment of the invention shows notches which have a generally triangular shape. However, it is readily apparent that the notches may also have other suitable configurations. For example, the notches may have a curvilinear or arcuate shape, and the inwardly located apex regions of the notches may terminate with a rounded shape instead of the pointed shape representatively shown in the figures.

In a particular aspect of the invention, notch 58 defines an acute angle, and preferably defines an acute angle which ranges from about 5°–45° to provide improved effectiveness. This acute angle is measured at the inwardly positioned apex region of the notch. In addition, the base measurement of notch 58 measured at the lateral, sideward facing opening of the notch at marginal contour 56 is less than 3 cm, and preferably ranges from about 0.5–2.5 cm to provide improved effectiveness.

In another aspect of the invention, primary absorbent layer 46 includes a plurality of spaced apertures 30 which extend at least partially through the absorbent layer. Apertures 30 provide recessed locations at which bonds may be formed through absorbent body 16 to interconnect selected layers of the garment, such as backsheet 12 and liner sheet 14. Apertures 30 also help to channel fluids away from the wearer's body and into the absorbent material of absorbent body 16. In the shown embodiment, the apertures are distributed over the surface area of primary absorbent layer 46 and have diameters within the range of about 0.1–1 cm. Preferably, apertures 30 have a diameter of about 0.3 cm to provide improved performance.

To provide increased garment conformability, apertures 30 can be selectively positioned and configured to define fold lines 60 which extend generally along the longitudinal direction 82 of the garment. Each fold line 60 is inwardly spaced from one of the marginal side contour lines of absorbent body 16 by approximately 15–35% of the width of the garment intermediate section. Preferably, the inward spacing of each fold line is about 27% of the width of the garment intermediate section. In the particular embodiment shown in FIG. 2, at least a portion of apertures 30 are positioned proximate to or even coincident with the apexes of selected notches 58 to define the fold lines. Thusly configured, absorbent body 16 can more readily flex along the fold lines toward the body of the wearer during use, and can thereby cooperate with notches 58 to provide greater conformability to the wearer's body contours. This increased flexibility can further contribute to the improved appearance of the garment and the improved resistance to leakage of fluids.

Supplemental absorbent layer 48 is positioned in facing relationship with primary absorbent layer 46, and is arranged for location more adjacent to the wearer's body in the shown embodiment. Alternatively, the supplemental layer can be located more remote from the wearer's body relative to the primary absorbent layer. In addition, supplemental layer 48 can be composed of material that is different than the material of primary layer 46. For example, primary layer 46 may be composed of a coform material and supplemental layer 48 may be composed solely of wood pulp fluff. Supplemental absorbent layer 48 has a smaller width than primary absorbent layer 46 along the garment cross direction 84. As a result, the supplemental absorbent layer defines a medial portion of absorbent body 16 which has a greater amount of absorbent material and a greater basis weight than the marginal sections of the absorbent body defined solely by primary layer 46. Supplemental absorbent layer 48 can also have a smaller length dimension along the garment longitudinal direction 82, and can be offset toward the "front" waistband section of the garment. As a result of this forward displacement of the increased amount of absorbent material, the medial "target" zone of absorbent body 16 can better absorb and retain a surge of liquid deposited therein. As illustrated in the Figures, the lateral extent of supplemental absorbent layer 48 is less than the lateral extent of primary absorbent layer 46 and does not extend beyond the fold lines 60 defined in the primary absorbent layer. Thusly configured, the supplemental absorbent layer substantially does not interfere with the flexing of primary absorbent layer 46 along these fold lines. The supplemental absorbent layer can also include longitudinal end portions with cross-directional widths greater than the cross-directional width of its middle crotch section. For example, the illustrated supplemental absorbent layer has a contour which defines an approximately dog-bone-shape planform.

In one aspect of the invention, supplemental absorbent layer 48 includes a plurality of apertures 30a to allow the bonding of selected garment layers therethrough and to more rapidly distribute liquids into the absorbent material. When employed, apertures 30a are positioned in a substantially coaxial registry with apertures 30 in primary absorbent layer 46. In other words, the central axes of the apertures are substantially aligned along the thickness dimension of the garment. Any desired bonding of the garment layers can then simultaneously extend through both supplemental absorbent layer 48 and primary absorbent layer 46. In a preferred embodiment of the invention, apertures 30a are configured with a greater diameter than the apertures 30. This provides a composite aperture 30c (FIG. 4) that has a generally tapered configuration, which is preferably wider at its body side end and narrower at its outerside end. For example, the diameter of apertures 30a can range from about 0.5–3.0 cm. In a particular aspect of the invention, the diameter of apertures 30a is about 2 cm to provide improved performance.

Figure 4:
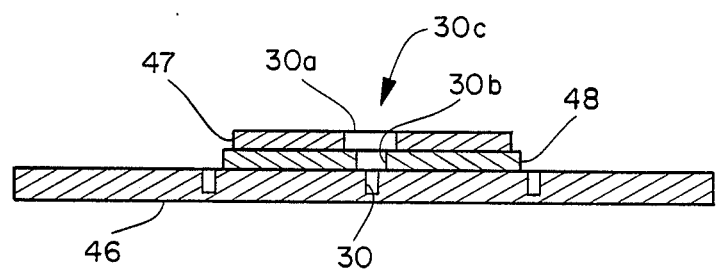
FIG. 4 representatively shows a cross-sectional view of an absorbent pad with a contoured cross-sectional profile.

The absorbent garment of the present invention can further include a middle absorbent layer 48 positioned between supplemental absorbent layer 47 and primary absorbent layer 46, as representatively shown in FIGS. 2 and 4. The middle absorbent layer can further increase the amount of absorbent material in the medial portion 42 of absorbent body 16, and can comprise a material that is different than or the same as the material employed to construct the primary and supplemental absorbent layers. This middle absorbent layer can have a greater longitudinal extent than supplemental absorbent layer 47, and should have a cross-directional width that does not extend past fold lines 60 defined in primary absorbent layer 46. In addition, middle absorbent layer 48 can have length less than the length of primary absorbent layer 46 and can include a middle crotch portion that is narrower than its longitudinal end portions to define an approximately dog-bone-shaped planform. The middle absorbent layer can also include a plurality of apertures 30b which extend at least partially therethrough. Preferably, apertures 30b extend completely through the middle absorbent layer and are located substantially in registry with apertures 30 and 30a. Apertures 30b are also preferably configured with a diameter less than the diameter of aperture 30a, but greater than the diameter of apertures 30. This configuration helps to maintain the generally tapered shape of the composite apertures formed into absorbent body 16.

When the three absorbent layers 46, 47 and 48 are employed, absorbent body 16 has a terraced cross-sectional profile, and defines three zones of increasing basis weight. In a particular embodiment of the invention the absorbent body is composed of wood pulp fluff, and Zone A, which includes only material from primary absorbent layer 46, has a basis weight of about 400 gm/m$^2$. Zone B includes material from both primary absorbent layer 46 and middle absorbent layer 47, and has a basis weight of about 800 gm/m$^2$. Zone C includes material from all three absorbent layers 46–48, and has a basis weight of about 1000 gm/m$^2$.

The previous description of contoured absorbent body 16 has been in the context of a combination of separate, distinct layers. However, it will be readily apparent that the contoured absorbent body can also comprise an integrally formed structure providing an equivalent cross-sectional profile. In addition, the tapered apertures 30c can be produced simultaneously with the formation of the integral, absorbent body structure.

In a further aspect of the invention, the disposable absorbent garment can be configured to provide a "quilted" absorbent structure, as representatively shown in FIG. 2. This quilt-like structure comprises a plurality of depressions or funnel pockets 62 which provide void areas extending into at least the medial portion of absorbent body 16. These void areas can better contain and retain semi-solid material, such as feces. As a result, funnel pockets 62 can help reduce leakage of feces past the edges of the garment. The funnel pockets also help to more rapidly conduct liquids into the absorbent body, and the quilted configuration can reduce undesired shifting and balling of the fibrous material comprising absorbent body 16.

Figure 5:
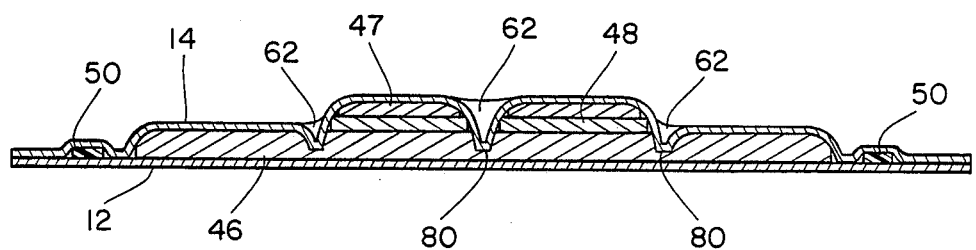
FIG. 5 shows a cross-sectional view of a representative contoured garment with funnel pockets formed therein.

To form funnel pockets 62, absorbent body 16 includes apertures 30c that extend at least partially therethrough, as illustrated in FIGS. 2 and 5. In addition, liner sheet 14 is composed of a thermally fusible material, such as spunbonded polyethylene. In one embodiment of the invention, liner sheet 14 is displaced and positioned into the apertures 30–30b and is interconnected to backsheet 12 with suitable bonding means, such as sonic bonds 80. Alternatively, the bonding means may comprise an adhesive bond or a mechanical interconnection employing an attachment member, such as a pin or stake.

In a more preferred embodiment of the invention, the garment includes a bonding layer 28 which is composed of a thermally fusible material and is interposed between backsheet 12 and absorbent body 16. Funnel pockets 62 can then be produced by sonically bonding liner sheet 14 to fusible bonding layer 28 through apertures 30c. With this configuration, the sonic bonds do not show on the outer surface of backsheet 12 and do not degrade the appearance of the garment outer surface. The number of funnel pockets 62 formed into absorbent body 16 is not critical. However, the larger the number of funnel pockets, the greater the stiffness of the absorbent body and the less conformable the garment may be to the body of the wearer.

In yet another aspect of the invention, the bonding layer can effectively be provided by a coform material which forms at least a portion of absorbent body 16. For example, the absorbent body can include a layer of fusible coform material on its outwardly facing side. Liner sheet 14 can then be sonically bonded to the layer of coform material through apertures 30–30b to form funnel pockets 62.

Funnel pockets 62, in the shown embodiment of the invention, are generally arranged along three distinct lines. The two side-most lines of funnel pockets are formed at the apertures that define the two fold lines 60, and a middle line of funnel pockets is formed approximately along the longitudinally extending centerline of the garment.

In an alternative arrangement of the invention, funnel pockets 62 are located along two generally longitudinally extending lines which intersect with notches 58. The liner sheet is displaced into selected portions of the notches, such as the notch apex regions, and suitably bonded or otherwise interconnected with another layer or portion of the garment to form the desired funnel pockets. This other garment portion may, for example, include backsheet 12, bonding sheet 28 or a section of coform material in absorbent body 16.

In still another aspect of the invention, at least one longitudinal end of absorbent body 16 has an indented recess formed into the terminal edge thereof, as representatively shown in FIG. 2. Preferably, an indented recess 64 is formed into each longitudinal end of the garment. The indented recess has a length 66 measured along the garment cross-direction 84 and has a depth measured along the garment longitudinal direction 82. The indented recess may have a rectilinear shape, as representatively shown by recess 64, or may have an arcuate, curvilinear-shaped outline, as representatively shown by recess 64a. In particular aspects of the invention, the indented recess is centrally positioned with respect to the diaper cross-direction, and the maximum depth 68 into the edge of the absorbent ranges from about 0.5–2.0 inches (1.27–5.08 cm). In addition, the length of recess 64 along the cross-direction 82 of diaper 10 is at least about 20% of the cross-directional width of the absorbent body waistband section. Preferably, recess 64 has a spanning length which is within about 30–60% of the cross-directional width of the absorbent body waistband section to provide improved effectiveness.

Recess 64 may be formed into absorbent body 16 employing various conventional manufacturing techniques. For example, the notch may be directly and simultaneously formed during the process of airlaying the cellulosic fibers to form the absorbent body. Alternatively, the recess can be cut out from the absorbent body after the absorbent body has been formed. Conventional devices, such as die cutters, can be employed to cut the absorbent body.

A waist elastic member 90 is attached to the waistband section of at least one of backsheet 12 and liner sheet 14. The elastic member is positioned substantially adjacent to the recess 64 formed into absorbent body 16, and is constructed and arranged to shir a portion of the garment waistband. Each waist elastic is secured at a position which is within recess 64 or closely adjacent to the recess. If waist elastic 90 is located outside of recess 64, the innermost edge of the elastic strip is preferably located within about 1 cm of the open end of the recess to provide the desired effectiveness. In the illustrated embodiment of the invention, the length of the waist elastic 90 is approximately coterminous with the lateral sideward edges of recess 64. If desired, however, waist elastic 90 may extend past or stop short of the sideward edges of the recess by a selected distance and still provide the desired effectiveness.

The combination of waist elastic 90 and recess 64 advantageously provides a configuration wherein the portions of the backsheet and liner sheet material within the area bounded by recess 64 are more readily shirred by the waist elastic 90 than the surrounding areas. The surrounding waistband areas are stiffer and firmer because of the absorbent material located therein. In contrast, the stiffer, firmer waistband regions located outside of recess 64 are relatively more resistant to the shirring effect produced by waist elastics 90. As a result, the tendency of the elasticized section of the waistband to tuck or curl inwardly toward the body of the wearer is effectively inhibited by the stiffer areas bordering recess 64. The garment waistband can then maintain a better fit against the body and present a more pleasing appearance.

Having thus described the invention in rather full detail, it will be readily apparent to a person having ordinary skill in the art that various changes and modifications may be made without departing from the spirit of the invention. All of such changes and modifications are contemplated as being within the scope of the invention as defined by the subjoined claims.

We claim:

1. An absorbent garment, comprising:
    a backsheet having waistband portions at each longitudinal end thereof, an intermediate portion interconnecting said waistband portions, and marginal portions along each lateral side edge thereof;
    a liquid permeable liner sheet which is located in facing relation with said backsheet;
    an absorbent body which is located between said backsheet and liner sheet, and which delimits waistband sections at least longitudinal end thereof, delimits an intermediate section interconnecting said waistband sections and delimits a marginal contour at each lateral side edge thereof, wherein each marginal side contour is interrupted by at least one collapsible notch section formed thereinto;
    fastening means for securing said garment on a wearer; and
    elastic members located adjacent to each of the notched side edges of said absorbent body extending generally along a longitudinal direction of the garment; wherein
    said elastic members are configured and arranged to form elasticized gathers at side margins of a garment intermediate section, and said marginal notch sections of said absorbent body are constructed to flex and close when said elastic members form a seal around the legs of the wearer.

2. An absorbent garment as recited in claim 1, wherein said absorbent body has a recess formed into at least one longitudinal terminal edge thereof, and wherein a waist elastic member is attached to said garment substantially adjacent to said recess for shirring a portion of the garment waistband.

3. An absorbent garment, as recited in claim 1, wherein said liner sheet is displaced into apex regions of said notches and interconnected with another portion of the garment to form pocket depressions.

4. An absorbent garment as recited in claim 1, wherein said absorbent body has a plurality of apertures formed at least partially therethrough, and said liner sheet is interconnected to said backsheet through said apertures.

5. An absorbent garment as recited in claim 1, further comprising a bonding layer which is located between said backsheet and said absorbent body; and wherein said absorbent body has a plurality of apertures formed at least partially therethrough, and said liner sheet is interconnected to said bonding layer through said apertures.

6. An absorbent garment as recited in claim 5, wherein said apertures are configured to define a plurality of quilt-like pocket depressions in at least a medial portion of said absorbent body.

7. An absorbent garment as recited in claim 1, wherein said backsheet and liner sheet are composed of thermally fusible material, said absorbent body has a plurality of apertures formed at least partially therethrough, and said liner sheet is fusibly interconnected to said backsheet through said apertures.

8. An absorbent garment as recited in claim 1, further comprising a bonding layer which is located between said backsheet and said absorbent body and is composed of a thermally fusible material; and wherein said liner sheet is composed of a thermally fusible material, said absorbent body has a plurality of apertures formed at least partially therethrough, and said liner sheet is fusibly interconnected to said bonding layer through said apertures.

9. An absorbent garment as recited in claim 8, wherein said apertures are configured to define a plurality of quilt-like pocket depressions in at least a medial portion of said absorbent body.

10. An absorbent garment as recited in claim 9, wherein said liquid permeable liner sheet has a plurality of apertures formed therethrough.

11. An absorbent garment as recited in claim 9, wherein said absorbent body has a recess formed into at least one longitudinal terminal edge thereof, and wherein a waist elastic member is attached to said garment substantially adjacent to said recess for shirring a portion of the garment waistband.

12. An absorbent garment as recited in claim 1, wherein said absorbent body has a contoured thickness with a greater amount of absorbent material in its medial portion than in its marginal edge regions.

13. An absorbent garment as recited in claim 12, wherein said absorbent body comprises:

a primary absorbent layer which defines waistband sections at each longitudinal end thereof and an intermediate section that which interconnects the waistband sections, and which defines a general marginal contour at each lateral side edge thereof;

a supplemental absorbent layer which is positioned in facing relationship with said primary absorbent layer, and which has a smaller cross-directional width and a smaller longitudinal length than said primary absorbent body having a greater amount of absorbent material therein.

14. An absorbent garment as recited in claim 13, further comprising a middle absorbent layer which is positioned between said primary absorbent layer and said supplemental absorbent layer, and which has a longitudinal length less than the length of said primary absorbent layer.

15. An absorbent garment as recited in claim 1, wherein said liquid permeable liner sheet has a plurality of apertures formed therethrough.

16. An absorbent garment, comprising:

a backsheet having waistband portions at each longitudinal end thereof, an intermediate portion interconnecting said waistband portions, and marginal portions along each lateral side edge thereof;

a liquid permeable liner sheet which is located in facing relation with said backsheet;

an absorbent body which is located between said backsheet and liner sheet, anhd which delimits waistband sections at each longitudinal end thereof, delimits an intermediate section interconnecting said waistband sections and delimits a marginal contour at each lateral side edge thereof, wherein each marginal side contour has at least one collapsible notch section formed therein, said absorbent body having a plurality of apertures which are formed at least partially therethrough and which define selected fold lines spaced inwardly from the marginal side contour lines of said absorbent body and extending generally along the longitudinal direction of the garment; and fastening means for securing said garment on a wearer.

17. An absorbent garment, comprising:

a backsheet having waistband portions at each longitudinal end thereof, an intermediate portion interconnecting said waistband portions, and marginal portions along each lateral side edge thereof;

a liquid permeable liner sheet which is located in facing relation with said backsheet;

an absorbent body which is located between said backsheet and liner sheet, and which delimits waistband sections at each longitudinal end thereof, delimits an intermediate section interconnecting said waistband sections and delimits a marginal contour at each lateral side edge thereof, wherein each marginal side contour has at least one collapsible notch section formed therein;

fastening means for securing said garment on a wearer; and a bonding layer which is located between said backsheet and said absorbent body and is composed of a thermally fusible material; wherein said liner sheet is composed of a thermally fusible material, said absorbent body has a plurality of apertures formed at least partially therethrough, said liner sheet is fusibly interconnected to said bonding layer through said apertures, said apertures are configured to define a plurality of quilt-like pocket depressions in at least a medial portion of said absorbent body, and said apertures are selectively positioned to define longitudinally extending fold lines which are inwardly located with respect to each marginal edge contour of said absorbent body.

18. An absorbent garment, comprising:

a backsheet having waistband portions at each longitudinal end thereof, an intermediate portion interconnecting said waistband portions, and marginal portions along each lateral side edge thereof;

a liquid permeable liner sheet which is located in facing relation with said backsheet and is composed of a thermally fusable material; and an absorbent body which is located between said backsheet and liner sheet, and which delimits waistband sections at each longitudinals end thereof, delimits an intermediate section interconnecting said waistband sections and delimits a marginal contour at each lateral side edge thereof, wherein said absorbent body includes a thermally fusable component therein and has a plurality of apertures formed partially therethrough, said liner is bonded to said thermally fusable absorbent body through said apertures to form quilt-like funnel pockets, and wherein said apertures define selected fold lines which are spaced inwardly from the marginal side contour lines of said absorbent body and extend generally along a longitudinal direction of the garment.

19. An absorbent garment as recited in claim 1, wherein said absorbent body comprises a thermally fusible coform material, said absorbent body has a plurality of apertures formed partially therethrough, and said liner is bonded to said coform material through said apertures to form quilt-like funnel pockets.

20. An absorbent garment, comprising:
   a backsheet having waistband portions at each longitudinal end thereof, an intermediate portion interconnecting said waistband portions, and marginal portions along each lateral side edge thereof;
   a liquid permeable liner sheet which is located in facing relation with said backsheet;
   an absorbent body which is located between said backsheet and liner sheet, and which delimits waistband sections at each longitudinal end thereof, delimits an intermediate section interconnecting said waistband sections and delimits a marginal contour at each lateral side edge thereof; and
   a bonding layer which is located between said backsheet and said absorbent body and is composed of a thermally fusible material; wherein
   said layer sheet is composed of a thermally fusible material,
   said absorbent body has a plurality of apertures formed at least partially therethrough,
   said liner sheet is fusibly interconnected to said bonding layer through said apertures,
   said apertures are configured to define a plurality of quilt-like pocket depressions in at least a medial portion of said absorbent body, and
   said apertures are selectively positioned to define longitudinally extending fold line which are inwardly located with respect to each marginal edge contour of said absorbent body.

* * * * *

UNITED STATES PATENT AND TRADEMARK OFFICE
CERTIFICATE OF CORRECTION

PATENT NO. : 4,762,521

DATED : August 9, 1988

INVENTOR(S) : T. H. Roessler, et al.

It is certified that error appears in the above-identified patent and that said Letters Patent is hereby corrected as shown below:

Column 5, line 9, delete "avar" and substitute therefor -- guar --.

Claim 1, column 10, line 32, delete "least" and substitute therefor -- each --.

Claim 16, column 12, line 4, delete "anhd" and substitute therefor -- and --.

Claim 17, column 12, line 23, delete "laterial " and substitute therefor -- lateral --.

Claim 18, column 12, line 62, delete "longitudinals" and substitute therefor -- longitudinal --.

Claim 20, column 14, line 8, delete "layer" and substitute therefor -- liner --.

Signed and Sealed this

Thirty-first Day of October, 1989

Attest:

DONALD J. QUIGG

*Attesting Officer*  *Commissioner of Patents and Trademarks*